(12) United States Patent
Held et al.

(10) Patent No.: US 7,638,115 B2
(45) Date of Patent: Dec. 29, 2009

(54) METHODS AND COMPOSITIONS FOR THE INTRODUCTION OF MOLECULES INTO CELLS

(75) Inventors: Bruce Marvin Held, Ames, IA (US); Herbert Martin Wilson, Ames, IA (US); Liming Hou, St. Louis, MO (US); Carol Jean Lewnau, Ames, IA (US); Janelle Christine Eby, Ames, IA (US)

(73) Assignee: Midwest Oilseeds, Inc., Adel, IA (US)

( * ) Notice: Subject to any disclaimer, the term of this patent is extended or adjusted under 35 U.S.C. 154(b) by 619 days.

(21) Appl. No.: 11/249,959

(22) Filed: Oct. 13, 2005

(65) Prior Publication Data

US 2006/0051870 A1 Mar. 9, 2006

Related U.S. Application Data

(60) Division of application No. 09/724,265, filed on Nov. 28, 2000, now Pat. No. 6,809,232, which is a continuation-in-part of application No. 09/450,226, filed on Nov. 29, 1999, now abandoned.

(51) Int. Cl.
*A61K 9/12* (2006.01)
*C13K 1/00* (2006.01)
*C12N 15/82* (2006.01)
*C12N 15/70* (2006.01)
*C12N 15/74* (2006.01)

(52) U.S. Cl. ............... 424/45; 800/293; 435/412; 435/415; 435/424; 435/426; 435/470; 435/471; 536/123.13

(58) Field of Classification Search ............... None
See application file for complete search history.

(56) References Cited

U.S. PATENT DOCUMENTS 3,854,321 A 12/1974 Dahneke
5,240,842 A 8/1993 Mets
5,455,240 A * 10/1995 Tuomanen et al. ............ 514/25
5,962,422 A * 10/1999 Nagy et al. .................... 514/25
5,976,880 A 11/1999 Sautter et al.
6,344,194 B1 * 2/2002 Sene et al. ................. 424/93.2
6,946,295 B2 * 9/2005 Polonenko et al. ......... 435/430.1

FOREIGN PATENT DOCUMENTS

| EP | 0/434616 A1 | 6/1991 |
| WO | WO 91/00915 A1 | 1/1991 |
| WO | WO 96/33270 A1 | 10/1996 |
| WO | WO 98/56894 A1 | 12/1998 |
| WO | WO 01 38514 A2 | 5/2001 |
| WO | WO 02 44391 A2 | 6/2002 |

OTHER PUBLICATIONS

Armstrong et al. Planta 164: 207-214.*
Cuddihy, A.E., et al., "Winged-bean protoplasts: isolation and culture to callus," *Plant Cell Tissue Organ Culture*, 1982, 1:201-209.
Fromm, Michael E., et al., "Inheritance and Expression of Chimeric Genes in the Progeny of Transgenic Maize Plants," *Bio/Technology*, Sep. 1990, 8:833-839.
Murashige, Toshio, et al., "A Revised Medium for Rapid Growth and Bio Assays with Tobacco Tissue Cultures," *Physiol. Plant*, 1962, 15:473-497.
Ranch, J.P., et al., "Plant Regeneration from Embryo-Derived Tissue Culture of Soybeans," *In Vitro Cellular & Developmental Biology*, Nov. 1985, 21:653-658.
Van Overbeek, J. et al., "Factors in Coconut Milk Essential for Growth and Development of Very Young Datura Embryos," *Science*, 1941, 94:350-351.
Watanabe, Kazuhiko, et al., "The growth promoting effect of phytic acid on callus tissues of rice seed," *Plant & Cell Physiol.*, 1971, 12:161-164.

* cited by examiner

*Primary Examiner*—David T Fox
(74) *Attorney, Agent, or Firm*—Jondle & Associates, P.C.

(57) ABSTRACT

The present invention is directed to the introduction of molecules, including nucleic acids, carbohydrates, plant growth regulators and peptides into cells and tissues. The present invention is also directed to media and methods for enhancing embryogenic callus production of elite lines of soybean.

16 Claims, 1 Drawing Sheet

METHODS AND COMPOSITIONS FOR THE INTRODUCTION OF MOLECULES INTO CELLS

CROSS REFERENCE

This application is a divisional of U.S. patent application Ser. No. 09/724,265 filed Nov. 28, 2000, now U.S. Pat. No. 6,809,232, which is a continuation-in-part of U.S. patent application Ser. No. 09/450,226, filed Nov. 29, 1999, now abandoned.

BACKGROUND OF THE INVENTION

The present invention is directed to a method for the introduction of molecules into cells, including but not limited to bacterial and plant cells. The molecules which are introduced by the method of the invention include, without limitation, nucleic acids, carbohydrates, plant growth regulators and peptides. The method of the invention is further directed to the transformation of bacteria and plant cells and tissues and to the resulting transformed cells and tissues. The present invention is also directed to a method and medium for initiating more rapid and uniform growth of embryogenic callus, specifically the growth of soybean embryogenic callus.

The publications, patents and other materials used herein to illuminate the background of the invention, and in particular cases, to provide additional details respecting the practice, are incorporated by reference, and for convenience are referenced in the following text by author and date and are listed alphabetically by author in the appended bibliography.

Delivery of Molecules to Cells

Small and large molecules can be efficiently delivered to cells without cell walls by electric pulsing (Dagher et al., 1991), electroporation (Fromm et al., 1986) or through mediation by polyethylene glycol (Klebe, R. J., et al., 1983). These technologies, however, are of limited use with plants due to the presence of the plant cell wall. Other methods have been developed specifically for DNA delivery to plant cells, such as particle bombardment (Sanford et al., 1987), silicon carbide whisker technology (Kaeppler et al., 1990), and electroporation (D'Halluin et al., 1992). However, each of these delivery methods has significant limitations. For example, particle bombardment, while reported effective for transformation of some plant cells, typically relies on precipitation of DNA molecules onto the surface of inert carrier particles prior to delivery. As a result, this requirement limits the usefulness of the technology for delivery of molecules such as proteins. In fact, there are no reports of effective delivery of proteins to plant cells using particle bombardment.

Silicon carbide whisker technology is reported to be much less efficient than particle bombardment for DNA delivery to plant cells and has been shown to be effective only in one cell type and single genotype of corn (Frame et al., 1994). Delivery of DNA to cells via electroporation has been described (D'Halluin et al., 1992; Laursen et al., 1994), however, this technology is ineffective for most cell types and there are very few reports of its successful use in plant transformation research. Furthermore, there are no known reports of its use to deliver proteins and other large molecules to the cells of higher plants.

Microinjection has been used to introduce proteins (Neuhaus et al., 1987) and DNA (Neuhaus, et al., 1987; U.S. Pat. No. 4,743,548) into plant cells. The principal limitations of microinjection are that it is extremely time-consuming and possible only with cells that can be isolated and handled as single entities. For these reasons microinjection has not been the method of choice for the transformation of any plant species where the goal is to produce genetically modified germplasm.

Current aerosol beam technology has been reported to be capable of transforming the chloroplast genome of *Chlamydomonas*, a unicellular, green alga (Mets, U.S. Pat. No. 5,240,842). *Chlamydomonas* chloroplast transformation can be considered a special situation since the chloroplast of *Chlamydomonas* is large, filling the entire cell of the typically 10 micron size organism. However, nuclear transformation was not reported by Mets and the only organism reported transformed was *Chlamydomonas*. Furthermore, in the eight years since the technology was first published, aerosol beam technology has not been reported to effect nuclear transformation of any species. Sautter et al. (1991) and U.S. Pat. No. 5,877,023, describe a technology which combines aspects of the aerosol beam and particle bombardment. Transformation with the technology reported by Sautter, et al., depends upon the inclusion of gold carrier particles of 1 micron diameter. There have been no other reports of the successful use of this technology.

As those of ordinary skill in the art recognize, it would be desirable to introduce a range of molecules including proteins and other macromolecules into plant and bacterial cells. This would allow, among other possibilities, the pursuit of pioneering studies in functional genomics. It is clear therefore that there is a need to improve aerosol beam technology to the point where it can be used routinely to effect nuclear transformation of important crop species such as corn and soybean and also to introduce other large macromolecules into cells. The method of the present invention solves this need.

Methods of Tissue Culturing

Cells which undergo rapid division and are totipotent are generally regarded as highly suitable targets for introduction of DNA as a first step in the generation of transgenic plants. Undifferentiated cells in tissues, such as meristematic tissues and embryogenic tissues are especially suitable. In general, cells of elite lines of crop plants are difficult to grow in culture. Specifically, cell division after introduction of nucleic acid is difficult to sustain and therefore selection of transformed cells often proves impossible.

Typically, embryogenic callus of soybean is cultured on high concentrations of 2,4-D (Ranch et al., 1985). However, even with high concentrations of 2,4-D in the culture medium, many cultivars do not produce sufficient embryogenic callus for transformation experiments. Specifically, there are no reports of high frequency initiation of callus from immature embryos or other tissue of elite soybean lines.

The useful lifetime of a soybean variety in the marketplace is usually around three years. This does not allow time for the backcrossing of transgenes into new and elite varieties from lines that are not elite, since by the time this could be accomplished, new varieties would have replaced those chosen as the recurrent parents in the backcrossing program. Furthermore, problems with loss of yield are commonly encountered when transgenes are introduced into elite material from non-elite transformants (Minor, 1998; Oplinger, 1998). Therefore, improved culture media which are capable of supporting rapid and uniform growth of a range of soybean germplasm would represent a significant advance in the art. Such an improved media are described herein.

SUMMARY OF THE INVENTION

The present invention is directed to a method for the introduction of molecules into cells, including but not limited to bacterial and plant cells. The molecules which are introduced by the method of the invention include, without limitation, nucleic acids, carbohydrates, plant growth regulators and peptides. The method of the invention is further directed to the transformation of bacteria and plant cells and tissues and to the resulting transformed cells and tissues. The present invention is also directed to a method and medium for initiating more rapid and uniform growth of embryogenic soybean callus, specifically the growth of elite lines of soybean.

DETAILED DESCRIPTION OF THE INVENTION

Figure 1:
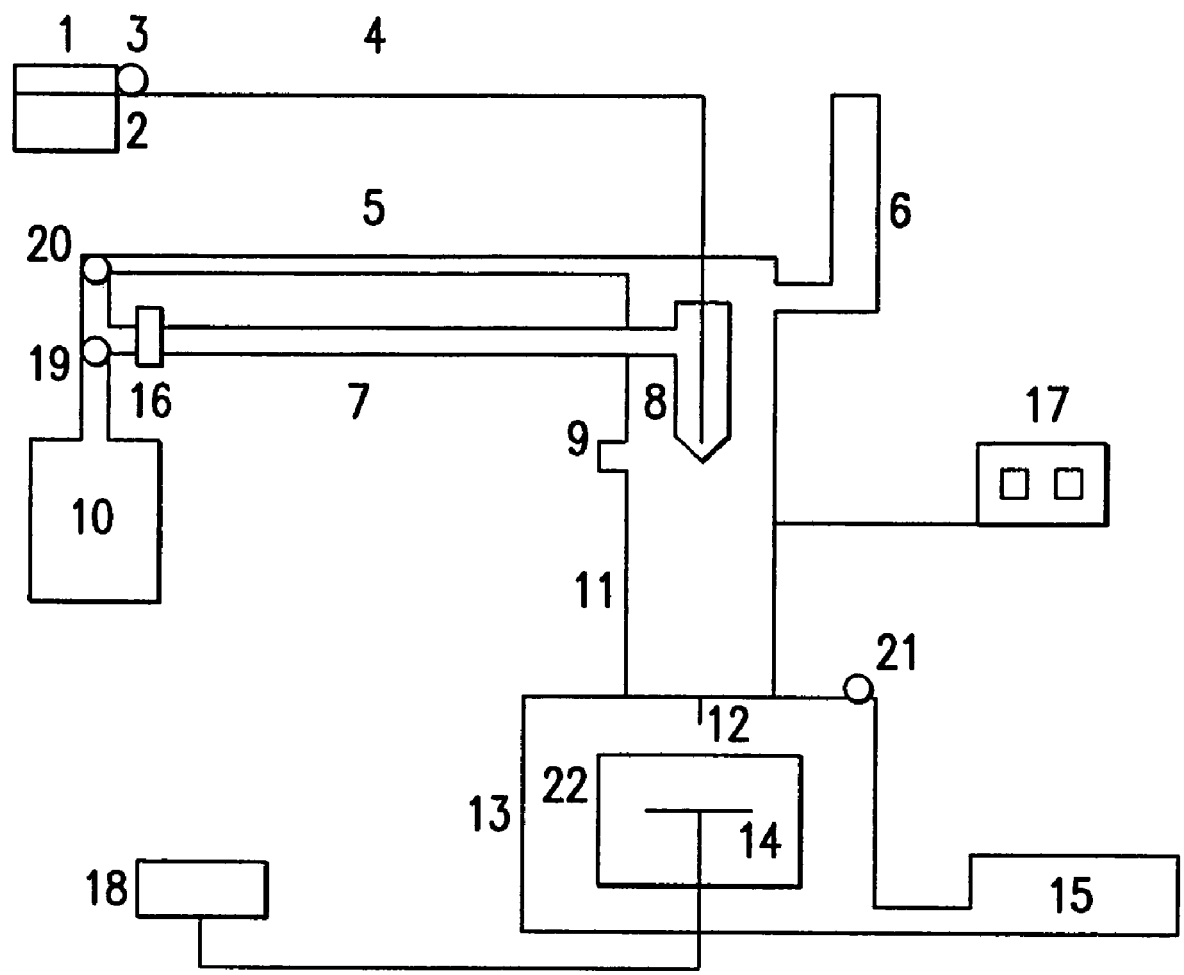
FIG. 1 is a schematic illustration of the aerosol beam apparatus of the present invention.

Using the method of the present invention it is possible to introduce molecules, including macro molecules, into cells without the need for precipitation of the molecules onto carrier particles, and therefore, it is not necessary to include protocols, such as precipitation, in order to associate the molecules with carrier particles. The present invention is especially useful for introducing peptides into large numbers of cells allowing for studies in such areas as functional genomics. The present invention can also be used to accomplish nuclear transformation of cells including but not limited to bacteria, and mono- and dicotyledonous plants. More particularly, elite germplasm of crop plant species can be transformed using the present invention. The present invention is further directed to media and methods for initiating rapid and uniform growth of elite lines of soybean, for example, transformed elite germplasm.

DEFINITIONS

The present invention employs the following definitions:

"Aerosol droplets" refer to droplets or particles, wet or dry, dispersed in a gas.

"Callus" refers to an undifferentiated mass of cells or tissue in vitro.

"Carrier particles" refer to gold or tungsten or other heavy metal particles ranging in size from 0.1 micron to 4 microns which are used to introduce molecules into cells.

"Continuous Targeting" refers to the delivery of aerosol droplets in a continuous stream toward a target.

"Elite Line" refers to a genetic line used in a product, or in the immediate (within three years) development of a product.

"Embryogenic Callus" refers to tissue composed of large numbers of somatic embryos or embryo-like structures.

"Exogenous Gene", "Exogenous DNA" and "Exogenous Nucleotide Sequence" refer to any gene, DNA or nucleic acid segment that is introduced into a recipient cell, regardless of whether a similar gene may already be present in such a cell.

"Germplasm" refers to varieties of genetic types within a species.

"Genotype" refers to the genetic identity of an organism.

"Microflow Nebulizer" refers to any device that creates an aerosol when provided with a sample flow rate, with or without use of a syringe pump, of between about 1 µl/minute and about 500 µl/minute.

"Nucleotide sequence" refers to a naturally occurring or non-naturally occurring nucleic acid, either isolated, synthesized or the result of genetic engineering techniques.

"Phytic Acid" refers to inositolhexaphosphoric acid.

"Stage" refers to the platform on which target cells may be placed in the method of the invention.

"Target Surface" refers to the cells comprising the uppermost layer of cells or tissue that is first encountered by the stream of aerosol droplets produced by the aerosol beam apparatus.

"Transformation" refers to the acquisition of new genetic coding sequences by the incorporation of an exogenous nucleotide sequence.

"Transgenic" and "Transformed" refers to organisms into which exogenous nucleotide sequences are integrated.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie and Fink, 1991; Gelvin et al., 1990; Grierson et al., 1984.

Method of Delivering Molecules to Cells

The method of the present invention offers a number of advantages over current methods of DNA delivery. Aerosol beam technology of the invention employs the jet expansion of an inert gas as it passes from a region of higher gas pressure to a region of lower gas pressure through a small orifice. The expanding gas accelerates aerosol droplets containing the molecules to be introduced into a cell or tissue. The size of the droplet is of particular importance when molecules are to be introduced into small cells or cellular organelles, for example, cells less than about 20 microns. The importance of droplet size has been demonstrated with particle bombardment technology where particles of greater than 1 micron in diameter were shown to be unsuitable for introducing DNA into cells of 10 to 20 microns in diameter (Klein, et al., 1988(a); Klein, et al., 1988(b) due to the damage produced by particles of such size. On the other hand, large particles have been reported to be more likely to penetrate the cells (U.S. Pat. No. 5,877,023).

Acceleration of droplets of a DNA containing solution by jet expansion is the subject of U.S. Pat. No. 5,240,842 to Mets which is herein incorporated by reference. The only successful transformation reported by Mets is with droplets of 2 micron diameter. Droplets of this size could be expected to destroy cells such as bacteria which are typically no larger than 2 microns. There are no examples of successful use of droplets smaller than 2 microns in diameter described in the patent to Mets. The diameter of a substantial portion of the aerosol droplets generated by the method of the invention are believed to be less than 0.1 microns at the point of impact with the target cells. This is supported by the ability to routinely and efficiently transform bacterial cells of approximately 1 to 2 microns in length using the method of the invention. Further support is found in the expectation that droplets larger than 0.1 micron in diameter are unlikely to be able to enter a rod-shaped or rectangular cell of 1 to 2 microns in length without destroying the cell.

Particle bombardment, as practiced using the Dupont PDS-1000, differs from aerosol beam technology in part because it relies on acceleration provided by a single burst of helium gas pressure. Viewed under a scanning electron microscope, the particles from the Dupont gun range in size from 0.1 microns up to 4 microns in diameter (using M5 tungsten particles with an average diameter of 0.4 microns).

DNA has been introduced into bacterial cells using polyethylene glycol (Klebe et al., 1983), electroporation (Bonmassie et al., 1990), treatment with divalent cations (Hanahan, 1983), and particle bombardment (Smith et al., 1992). Smith et al. (1992), consider convenience to be one of the main advantages of biolistic transformation over electroporation. Nevertheless, to achieve efficient transformation using the biolistic process, treatment of bacterial cells with an osmoticum is required as is careful control of the relative humidity at which the particles were stored prior to bombardment. Bacterial transformation using the method of the present invention is much more efficient than biolistic-mediated transformation and requires no special pretreatments.

Based on successful and efficient transformation of bacteria using the method of the present invention, it is believed that a substantial number of the aerosol droplets produced are less than 0.1 micron in diameter at the point of impact with the target cells. DNA carried in aerosol droplets of this small size penetrates cells only because of the speeds attained by the aerosol droplets. Speeds achieved by the aerosol beam method of the invention are supersonic and can reach 2000 meters/second. By contrast, top speed achieved by the particle gun is 200 meters/second.

In part, because aerosol droplets generated by the present invention are so much smaller than the particles produced by the prior art, the present invention is superior in delivering molecules to small cells, for example cells less than 20 microns in diameter. Many animal, plant and microbial cells are in this size range. Entry of micron-size particles into cells of this size can be expected to cause significant damage. The very small aerosol droplets produced by the method of the present invention are also advantageous for chloroplast transformation, particularly in monocots and graminaceous embryogenic cell cultures contain proplastids (the target for chloroplast transformation) that are typically less than 1 micron in diameter (Bilang and Potrykus, 1998).

Another advantage of the present invention is that it permits better quantification of DNA delivery to cells than is possible with particle gun technology. This is because no precipitation or coating of DNA onto carrier particles is required with the method of the invention, procedures which introduce variability into the DNA delivery process.

As a further embodiment of the present invention, molecules other than DNA can be readily introduced into cells, either alone or in combination with DNA. Inclusion of molecules other than DNA introduced at the same time as DNA could improve integration and increase the number of selectable transformants. By contrast, effective delivery of molecules can be achieved with particle bombardment only after first coating the particles with the substance to be delivered. In those cases where it is not possible or desirable to use coated particles, the aerosol beam may be the most effective way to deliver chemicals directly to the interior of cells on a large scale.

An additional advantage of the present invention is that DNA is delivered as a stream of aerosol droplets emerging through a small orifice (continuous targeting). This targeting can continue for as long as the target tissue can survive being held in a vacuum. In the course of delivery the droplet stream can then be precisely targeted. This further distinguishes aerosol beam technology from particle bombardment as currently practiced where all DNA-coated particles are delivered to cells in a single blast resulting in a shot pattern covering an area of several centimeters in diameter. A hybrid of the aerosol beam and particle bombardment methods (Sautter, et al.; U.S. Pat. No. 5,877,023) is reported to deliver a solution of DNA and 1 micron diameter gold carrier particles in interrupted blasts, thus continuous targeting of tissue is not possible with this method. Continuous targeting also allows for the identification of an area of tissue (such as the apex of a shoot meristem) and its positioning under the beam to ensure focused delivery of aerosol droplets to the tissue. Furthermore, repeated blasts which are delivered with particle bombardment and the method of Sautter, et al., can be expected to result in severe and extensive tissue destruction. The ability to continuously target cells or tissues makes the aerosol beam clearly superior to other direct DNA delivery methods including particle bombardment.

The aerosol beam of the present invention differs from U.S. Pat. No. 5,240,842 in numerous respects. First, Mets does not include any positive pressure entrainment airflow to guide or focus the aerosol beam. Second, Mets includes a vent in the compressed gas path to allow release of excess aerosol. This results in wasted compressed gas and aerosol material. The vent is required in Mets because of the high flow rates used. Third, the nebulizer used by Mets is a type used in inhalation therapy and is described as of the Lovelace design. This nebulizer is a single use disposable unit that generates aerosol droplets with median mass diameters in the range of 2 microns. Commercially available nebulizers such as HEN or MCN100 were used in example. However, any microflow nebulizer, as defined herein, can be used in the practice of the present invention. Unexpectedly, use of microflow nebulizers cacilitated insertion of molecules into cells. Fourth, the preferred embodiment of the present invention includes a syringe pump which regulates the flow rate of the sample to the nebulizer. Fifth, droplets of the size described by Mets would be too large to deliver DNA or any other molecule to most bacteria or plant cells and yet allow survival of these cells.

Transformation of Plant Cells and Tissues

Introduction of DNA and other molecules such as proteins into plant cells by the method of the present invention is exemplified by transformation of corn (monocotyledonous plants) and soybean (dicotyledonous plants). Briefly, the transgenic plants of this invention may be produced by (I) culturing a source of cells, (II) optionally, pretreating cells to yield tissue with increased capacity for uptake and integration by aerosol beam technology, (III) transforming said tissue with an exogenous nucleotide sequence by the aerosol beam method of the invention, (IV) optionally, identifying or selecting for transformed tissue, (V) regenerating transgenic plants from the transformed cells or tissue, and (VI) optionally, producing progeny of said transgenic plants.

Method of Culturing Cells

Corn Cell Cultures.

The corn cells which may be used as starting materials in the present transformation process include elite inbred lines of corn. For example, embryogenic callus and immature embryos of Stine Inbred 963 were used for both transient expression experiments and the production of stably transformed callus, embryos and plants. Other cells may be used, including those derived from meristems. These meristems are found, for example, in juvenile leaves, immature tassels, immature and mature embryos and coleoptilar nodes. While the method of the present invention can be applied to any corn cells from which fertile plants can be recovered, cell cultures derived from immature embryos or embryogenic callus have been utilized herein for purposes of example.

Methods of preparing and maintaining corn cells are well known in the art (Duncan et al., 1985). Typically, cultures are prepared from immature maize embryos which have been removed from the kernels of an ear when the embryos are about 1-2 mm. in length. The scutellum of immature embryos can be stimulated to give rise to embryogenic callus from which plants can be regenerated. Embryogenic callus can also be obtained from the developing reproductive organs of a corn plant. Exemplary methods for isolating immature embryos from corn are described by Green and Phillips (1976).

In a preferred embodiment of the invention, the embryos were placed on culture medium, for example, DN62AG (Table 1), under aseptic conditions. This culture medium, DN62AG, has been described in U.S. Ser. No. 09/203,679, filed December, 1998, incorporated herein by reference. It has been discovered that immature embryos incubated for approximately 2 to 3 days on DN62AG medium, after dissection and prior to beaming, show improved survival. This, in turn, improves the efficiency with which transformants can be recovered. The embryogenic callus cultures are routinely maintained on stock culture medium, preferably on DN62 (Table 1) for ten-day periods between transfers.

Soybean Cell Cultures.

Soybean cells which can be used as starting materials in the method of the invention include cell cultures and explants containing meristematic tissue from which plants can be regenerated. Exemplary of cells which are appropriate are embryogenic callus of Stine 13404-TT (Examples 10).

Conventional methods of preparing and maintaining embryogenic soybean cultures are described by Ranch et al. (1985). In one embodiment of the invention, the medium of Ranch et al (1985), can be modified by the inclusion of one or more of four constituents (Example 8). Immature cotyledons about 1 mm in length were used as the initial explants and were placed on culture media under sterile conditions.

In another embodiment of the present invention, a novel culture media may be used to stimulate high frequency production of embryogenic soybean callus. Improvement varied with the genotype being cultured. The length of time required for a culture passage was unexpectedly reduced to two weeks with the use of this novel medium as compared to four weeks typical with other media. The inclusion of one or more of four media constituents, coconut water, myoinositol, phytic acid and inorganic phosphate concentration, enhanced embryogenic callus production and allowed significant improvements to be made to transgenic clone production in terms of number of clones recovered, embryo morphology, and reduction in the time needed to identify the clones and regenerate plants from them. The medium of Ranch et al., 1985 (referred to herein as B1-30) was used as the basal medium. An example of the medium of the present invention is B1-30 3Co5My0.25PA0.5K (footnote, Table 5). Although this medium is a preferred embodiment of growth medium, other conventional media may be utilized in the practice of the invention.

Pretreatment of Cells

In another embodiment of the present invention, pretreatment of the cells may be carried out in order to increase nucleic acid delivery using the method of the invention. For example, corn cells can be osmotically stressed to improve DNA delivery while preserving cell viability. Possible methods of osmotic stress include those conventional methods known in the art, for example, Russell et al., 1992. As a preferred embodiment of the invention, a novel medium designed to provide osmotic stress referred to as DN62OSM was used (Example 2, Table 1). The duration of exposure to osmotic stress may range from about 45 minutes up to about 24 hours on this medium, with a preferred duration of about 45 minutes to about one hour. In the case of soybean cells an osmotic pretreatment was not employed.

Introduction of Nucleic Acid into Cells

One embodiment of the present invention is directed to the introduction of a nucleotide sequence into plant cells via aerosol beam technology. Once a desired nucleotide sequence has been synthesized or cloned, and engineered, it is necessary to integrate it into the genome of a plant of interest so that it is stably inherited by progeny of the transformed plant. Following introduction of foreign sequence into target cells and subsequent cell division, selection is applied to identify those cells in which integration and expression of the sequence is occurring. Stable transformation involves the integration of functional genetic sequences into the genome so that the integrated sequences are passed on to and are present in the transformed plants. Any procedure which could enable the stable integration of nucleic acids would greatly improve transformation protocols. In contrast, transient transformation results in eventual loss of the sequence and, therefore, transient methods are of little use in generating transgenic plants, although they may be of use in the optimization of conditions for stable transformation and in evaluation of gene expression.

An embodiment of the aerosol beam apparatus of the present invention is shown in FIG. 1. The apparatus includes a pressurized gas supply 10, a vacuum chamber 13, and an entrainment housing 11.

The pressurized gas supply 10 may contain a pressurized propellant gas such as, for example, helium. The pressurized gas supply 10 is connected to a microflow nebulizer conduit 7 and is also connected to an entrainment tube 5.

The entrainment housing 11 has an interior, and located within the interior is all or a portion of a microflow nebulizer 8. The entrainment housing 11 interior communicates with the pressurized gas supply 10 via the entrainment tube 5, which may include a pressure regulator 20. The microflow nebulizer 8 communicates with the pressurized gas supply 10 via the microflow nebulizer conduit 7, which may include a filter 16 and a pressure regulator 19. A single regulator may be employed if the entrainment gas pressure can be the same as the nebulizer gas pressure. The entrainment housing 11 may also include a temperature controller 17 which controls the temperature in the entrainment housing 11 to a range of about 32 degrees to about 80 degrees Centigrade. A pressure gauge 6 is connected to the entrainment housing 11 and may be used to control the pressure regulator 20 to set the entrainment air pressure and flow. The entrainment housing 11 may include a nucleospot 9. The nucleospot 9 may be used to reduce electrostatic charges created by the moving gas.

The microflow nebulizer 8 is an aerosol nebulizer that is fed both a sample material and a pressurized gas. The sample material may be fed to the microflow nebulizer 8 by a pump or other suitable means. In the microflow nebulizer 8, the pressurized gas forces the sample material through a small orifice in the nebulizer, where the pressurized gas converts the sample material into aerosol droplets. The aerosol droplets are then carried by the resulting beam of gas to the nozzle, through which the aerosol droplets greatly accelerated.

A sample material supply conduit 4 is connected to the microflow nebulizer 8. The sample material supply conduit 4 may be further connected to a pump 2 and filter 3. In a preferred embodiment, the pump 2 is a syringe pump and includes a plastic syringe 1 holding a quantity of an sample material.

In addition to the aerosol beam, pressurized helium flows into the entrainment housing 11 through the entrainment tube 5. This entrainment gas flow also has a velocity and moves substantially parallel to the aerosol spray, and serves to entrain the aerosol spray and focus it on the way to the target.

The vacuum chamber 13 includes a nozzle 12, a vacuum pump 15, and a door 22. The vacuum chamber 13 may additionally include a stage 14, a vacuum gauge 21, and a stage switch 18. The nozzle 12 further guides the aerosol beam as it approaches the stage 14 (on which the target to be injected rests). The nozzle 12 includes an orifice, with the orifice size ranging from about 200 microns to about 500 microns. The orifice size is preferably 300-330 microns. The combination of the pressurized gas in the entrainment housing 11 and the partial vacuum in the vacuum chamber 13 accelerates the aerosol droplets that impact the target cells.

The stage 14 may be a movable stage wherein the target may be moved relative to the incoming aerosol spray so that a controlled area may be impacted with the sample material. The stage switch 18 may be used to control movement of the stage 14. The vacuum gauge 21 may be used to monitor and control the vacuum level in the vacuum chamber 13.

The aerosol can be produced by various microflow nebulizers known in the art, such as the HEN from J. E. Meinhard Associates, Inc., or the MCN100 style M-4 nebulizer from Cetac Technologies, Inc., although other microflow nebulizers may also be used. The preferred nebulizer described in U.S. Pat. No. 5,240,842 was one typically used in inhalation therapy and was described as being of the Lovelace design which is a single-use disposable unit that generates aerosol droplets with median mass diameters in the range of 2 microns.

The nebulizing gas can be selected from those inert gases known in the art, preferably high purity compressed helium. The gas is regulated and filtered. The entrainment gas can be high purity compressed helium, filtered or not. The entrainment tube or housing may contain a nucleospot to reduce electrostatic charges and can be maintained at a temperature of between about 32 and 80° C. by temperature controllers. The sample flow rate may be set at from about 1 to about 1200 µl/min.

The method of the present invention differs from the several embodiments described in Mets (U.S. Pat. No. 5,240,842) wherein a common feature was the presence of a vent to allow release of excess aerosol which was the result of the high flow rates that were used. It has been unexpectedly discovered that high efficiency microflow nebulizers, such as the HEN and MCN 100, provide adequate aerosol droplet production when using very low (1 to 350 µl/min) flow rates. Venting of excess aerosol is therefore not necessary with the method of the invention. Furthermore, the aerosol droplets produced by the microflow nebulizers in the method of the invention are much smaller at the point of impact with the target than the 2 micron diameters preferred by Mets. Small droplet size can be maintained in the method of the invention by the use of helium as the nebulizing gas although other means known in the art may be used.

Improved efficiency of transformation is possible using the method of the invention which employs the routine production of small aerosol droplets traveling at supersonic speed. The correlation between the reduced droplet size and improved efficiency was unexpected. It was previously reported in U.S. Pat. No. 5,877,023, in regard to particle size, that large particles are more able to penetrate the cells though use of small particles is more favorable for the survival of cells (Col. 7, L. 14-18). The method of the invention also improves upon existing technology by enabling the routine transformation of bacteria.

The chamber vacuum can be maintained at from about 26 to about 30 in. Hg throughout a given run with use of a vacuum pump. Water may be placed in the vacuum chamber to prevent loss of moisture from the target tissue. A syringe needle cut off just proximal to the plastic holder can be used for the nozzle. Nozzle diameters of from about 200 to about 500 microns can be used. The target tissue can be placed in the center of an agar plate below the nozzle tip. The stage movement can be adjusted to achieve the desired result.

Briefly, treatment of target tissue with the aerosol beam apparatus may be performed as follows: (1) place tissue on target surface, on the stage; (2) start the vacuum pump; (3) set the nebulizing gas pressure; (4) set the entrainment gas pressure; (5) start the syringe pump; (6) start the movement of the stage and let it run while the aerosol particles suspended in the inert gas impact the target tissue. Delivery can continue for as long as the target tissue can survive being held in a vacuum.

In order to successfully produce stably transformed plants by aerosol beam technology, four requirements must be met: (1) the target cells must remain viable; (2) the target cells must be able to take up the recombinant nucleic acid at high enough frequencies to insure the stable transformation of a useful number of cells; (3) once transformed, the recipient cells must be able to maintain cell division and regenerative capacity throughout the selection process in order to confirm and identify stably transformed cells; and (4) the transformed regenerated plants must be able to express the recombinant nucleic acid.

Utilizing the method of the present invention, accurate and extensive tissue targeting can be achieved with any explant, including immature embryo, immature tassel, section of leaf or root, anther, pollen and meristem cells of corn, and meristem and somatic embryo cells of soybean. For example, in the case of corn, pollen, as well as its precursor cells, microspores, may be capable of functioning as recipient cells for nucleic acid delivery, or as vectors to carry foreign nucleic acid for incorporation during fertilization. The continuous targeting which is possible with the method of the invention enables flexibility and accuracy in delivering nucleic acid to target cells. Individual immature corn embryos can be targeted so that only particular regions of the scutellum are subjected to the aerosol beam or, alternatively, it is possible to deliver nucleic acid to the entire surface area of the scutellum with the aerosol beam.

Examples of genes useful for expression in transformed plant cells are known in the art. More particularly, plants can be genetically engineered to express various phenotypes of agronomic interest. Such genes include, but are not limited to, those described herein.

Genes That Confer Resistance or Tolerance to Pests or Disease (A) Plant disease resistance genes. Plant defenses are often activated by specific interaction between the product of a disease resistance (R) gene in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium fulvum* (Jones et al. (1994)), the tomato Pto gene, which encodes a protein kinase, for resistance to *Pseudomonas syringae* pv. tomato (Martin et al. (1993)), and the *Arabidopsis* RSSP2 gene for resistance to *Pseudomonas syringae* (Mindrinos et al. (1994)).

(B). A *Bacillus thuringiensis* protein, a derivative thereof or a synthetic polypeptide modeled thereon, such as, a nucleotide sequence of a Bt δ-endotoxin gene (Geiser et al. (1986)). Moreover, DNA molecules encoding δ-endotoxin genes can be purchased from American Type Culture Collection (Rockville, Md.), under ATCC accession numbers. 40098, 67136, 31995 and 31998.

(C) A lectin, such as nucleotide sequences of several *Clivia miniata* mannose-binding lectin genes (Van Damme et al. (1994)).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include a rice cysteine proteinase inhibitor (Abe et al. (1987)), a tobacco proteinase inhibitor I (Huub et al. (1993)), and an α-amylase inhibitor (Sumitani et al. (1993)).

(F) An insect-specific peptide or neuropeptide which, upon expression, disrupts the physiology of the affected pest. Examples of such genes include, an insect diuretic hormone receptor (Regan (1994), an allostatin identified in *Diploptera puntata* (Pratt (1989)), insect-specific, paralytic neurotoxins (U.S. Pat. No. 5,266,361).

(G) An insect-specific venom produced in nature by a snake, a wasp, etc., such as, a scorpion insectotoxic peptide (Pang (1992)).

(H) An enzyme responsible for a hyperaccumulation of a monoterpene, a sesquiterpene, a steroid, hydroxamic acid, a phenylpropanoid derivative or another non-protein molecule with insecticidal activity.

(I) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al. (1993)) and parsley ubi4-2 polyubiquitin gene (Kawalleck et al. (1993)).

(J) A molecule that stimulates signal transduction. Examples of such molecules include, nucleotide sequences for mung bean calmodulin cDNA clones (Botella et al. (1994)), a nucleotide sequence of a maize calmodulin cDNA clone (Griess et al. (1994)).

(K) A hydrophobic moment peptide. See U.S. Pat. Nos. 5,659,026 and 5,607,914, the latter teaches synthetic antimicrobial peptides that confer disease resistance.

(L) A membrane permease, a channel former or a channel blocker, such as, a cecropin-β lytic peptide analog (Jaynes et al. (1993)) which renders transgenic tobacco plants resistant to *Pseudomonas solanacearum*.

(M) A viral protein or a complex polypeptide derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al. (1990).

(N) An insect-specific antibody or an immunotoxin derived therefrom. Thus, an antibody targeted to a critical metabolic function in the insect gut would inactivate an affected enzyme, killing the insect. For example, Taylor et al. (1994) shows enzymatic inactivation in transgenic tobacco via production of single-chain antibody fragments.

(O) A virus-specific antibody. See, for example, Tavladoraki et al. (1993), which shows that transgenic plants expressing recombinant antibody genes are protected from virus attack.

(P) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al. (1992)). The cloning and characterization of a gene which encodes a bean endopolygalacturonase-inhibiting protein is described by Toubart et al. (1992).

(O) A developmental-arrestive protein produced in nature by a plant, such as the barley ribosome-inactivating gene, have increased resistance to fungal disease (Longemann et al. (1992)).

Genes That Confer Resistance or Tolerance to a Herbicide (A) A herbicide that inhibits the growing point or meristem, such as an imidazalinone or a sulfonylurea. Exemplary genes in this category code for mutant ALS (Lee et al. (1988)) and AHAS enzyme (Miki et al. (1990)).

(B) Glyphosate (resistance imparted by mutant EPSP synthase and aroA genes) and other phosphono compounds such as glufosinate (PAT and bar genes), and pyridinoxy or phenoxy proprionic acids and cyclohexones (ACCase inhibitor encoding genes). See, for example, U.S. Pat. No. 4,940,835, which discloses the nucleotide sequence of a form of EPSP synthase which can confer glyphosate resistance. A Nucleic acid molecule encoding a mutant aroA gene can be obtained under ATCC accession number 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthase genes which confer resistance to herbicides such as L-phosphinothricin. The nucleotide sequence of a phosphinothricin acetyltransferase gene is provided in European application No. 0 242 246. De Greef et al. (1989) describes the production of transgenic plants that express chimeric bar genes coding for phosphinothricin acetyltransferase activity. Exemplary of genes conferring resistance to phenoxy proprionic acids and cyclohexones, such as sethoxydim and haloxyfop, are the Acc1-S1, Acc1-S2 and Acc1-S3 genes described by Marshall et al. (1992).

Genes that Confer Resistance or Tolerance to Environmental Stresses (A) Cold, freezing or frost. This includes genes that code for proteins that protect from freezing and for enzymes that synthesize cryoprotective solutes. Examples of such genes are *Arabidopsis* COR15a (Artus et al. (1996)) and spinach CAP160 (Kaye et al. (1998)). Also in this category are regulatory genes that control the activity of other cold tolerance genes (Tomashow and Stockinger (1998)).

(B) Drought or water stress. Kasuga et al. (1999) report how stress inducible expression of DREB1A in trangenic plants increases their tolerance of drought stress. Pilin-Smits et al. (1998) report that expression of baterial genes for synthesis of trehalose produces tolerance of water stress in transgenic tobacco.

(C) Salinity or salt stress. Genes that code for proteins that minimize uptake of sodium in the presence of high salt, or cause the plant to sequester sodium in vacuoles, can enable plants to tolerate higher levels of salt in the soil. The wheat HKT1 potassium transporter, described by Rubio et al. (1999), is an example of the former. Apse et al. (1999) describe how an *Arabidopsis* $Na^+/H^+$ antiporter can act in the latter manner.

(D) Metals. Protection from the toxic effects of metals such as aluminum and cadmium can be accomplished by transgenic expression of genes that prevent uptake of the metal, or that code for chelating agents that bind the metal ions to prevent them from having a toxic effect. Examples of such genes are *Arabidopsis* ALR104 and ALR108 (Larsen et al. (1998)) and genes for the enzymes involved in phytochelatin synthesis (Schafer et al. (1998)).

Genes That Confer or Contribute to a Value-Added Trait (A) Modified fatty acid metabolism, for example, by transforming maize or *Brassica* with an antisense gene or stearoyl-ACP desaturase to increase stearic acid content of the plant (Knultzon et al. (1992)).

(B) Decreased phytate content (1) Introduction of a phytase-encoding gene would enhance breakdown of phytate, adding more free phosphate to the transformed plant, such as the *Aspergillus niger* phytase gene (Van Hartingsveldt et al. (1993)).

(2) A gene could be introduced that reduces phytate content. In maize, for example, this could be accomplished by cloning and then reintroducing DNA associated with the single allele which is responsible for maize mutants characterized by low levels of phytic acid (Raboy et al. (1990)).

(C) Modified carbohydrate composition effected, for example, by transforming plants with a gene coding for an enzyme that alters the branching pattern of starch. Examples of such enzymes include, *Streptococcus* mucus fructosyltransferase gene (Shiroza et al. (1988)), *Bacillus subtilis* levansucrase gene (Steinmetz et al. (1985)), *Bacillus licheniformis* α-amylase (Pen et al. (1992)), tomato invertase genes (Elliot et al. (1993)), barley amylase gene (Søgaard et al. (1993)), and maize endosperm starch branching enzyme II (Fisher et al. (1993)).

(D) Modified lignin content. The amount or composition of lignin can be altered by increasing or decreasing expression of the biosynthetic enzymes for phenylpropanoid lignin precursors, such as cinnamyl alcohol dehydrogenase (CAD), 4-coumarate:CoA ligase (4CL), and O-methyl transferase (OMT). These and other genes involved in formation of lignin are described in Bloksberg et al. (1998).

As those of ordinary skill in the art will recognize, this is only a partial list of possible genes that can be used with the transformation method of the present invention. Synthesis of genes suitably employed in the present invention can be effected by means of mutually priming long oligonucleotides. See, for example, Ausubel et al. (1990) and Wosnick et al. (1987). Moreover, current techniques which employ the polymerase chain reaction permit the synthesis of genes as large as 6 kilobases in length or longer. See Adang et al. (1993) and Bambot et al. (1993). In addition, genes can readily be synthesized by conventional automated techniques.

As those of ordinary skill in the art will also recognize, regulatory sequences including promoters, terminators and the like will also be required, and these are generally known in the art (Zhao et al. (1998)). Plant expression cassettes preferably comprise a structural gene to which is attached regulatory DNA regions that permit expression of the gene in plant cells. The regulatory regions consist at a minimum of a promoter capable of directing expression of a gene in a plant cell. The promoter is positioned upstream or at the 5' end of the gene to be expressed. A terminator is also provided as a regulatory region in the plant expression cassette and is capable of providing polyadenylation and transcription terminator functions in plant cells. The terminator is attached downstream or at the 3' end of the gene to be expressed. Marker genes, included in the vector, are useful for assessing transformation frequencies in this invention.

The nucleic acid to be delivered to cells may contain selectable marker sequences under control of appropriate recognizable promoters for use in selecting transformed cells. Numerous selectable marker genes are available for use in plant transformation including, but not limited to, neomycin phosphotransferase II, hygromycin phosphotransferase, EPSP synthase and dihydropteroate synthase. See, Miki et al. (1993). Other markers and promoters are well known in the art. The vectors may also contain selectable marker sequences under control of appropriate recognizable promoters for use in selecting transformed cells. Suitable markers and promoters are well known in the art.

The recombinant nucleic acid used for transformation herein may be circular or linear, double-stranded or single-stranded. Generally, the nucleic acid is in the form of a recombinant plasmid and contains coding regions of beneficial heterologous nucleic acid with flanking regulatory sequences which promote the expression of the nucleic acid in the genome of the transformed plant. For example, the recombinant nucleic acid may itself comprise or consist of a promoter that is active in other genotypes, or may utilize a promoter already present in the genotype that is the transformation target.

The compositions of, and methods for, constructing a nucleic acid sequence which can transform certain plants are well known to those skilled in the art, and the same compositions and methods of construction may be utilized to produce the recombinant nucleic acid useful herein (J. Sambrook et al., *Molecular Cloning: A Laboratory Manual*, Cold Spring Harbor Laboratory Press (2d), 1989). The specific composition of the nucleotide sequence is not central to the present invention and the invention is not dependent upon the composition of the specific transforming nucleotide sequence which is used.

Restriction enzymes can be introduced, using the method of the invention, along with linear nucleic acid having compatible cohesive ends to increase the frequency of transformants. The introduction of restriction enzymes andn via electroporation has been reported for yeast and Dictyostelium (Schiestl and Petes, 1991; Kuspa and Loomis, 1992). However similar results have not previously been reported with plant transformation.

Selection of Transformed Cells

After beaming, the tissue may be retained on the osmoticum or shortly thereafter transferred to a recovery medium. Following recovery, it is desirable to identify and select those cells which contain the exogenous nucleic acid. There are two general approaches which have been found useful for accomplishing this. First, the transformed cells can be screened for the presence of the recombinant nucleic acid by various standard methods which could include assays for the expression of reporter genes, use of probes for or amplification of the desired nucleotide sequence and assessment of phenotypic effects of the recombinant nucleic acid, if any. Alternatively and preferably, when a selectable marker or reporter gene has been transmitted along with or is part of the recombinant nucleic acid, those cells which have been transformed can be identified by detecting expression of the selectable marker or reporter genes. For example, transient expression may be evaluated by use of the GUS expression cassette containing the GUS gene, which encodes an enzyme for which various chromogenic substrates are known. Stable transformation may be evaluated by use of the bar expression cassette. Various other selection schemes for identification of stably transformed tissue may be used, including selection on bialaphos or use of the GFP gene in combination with the *Streptomyces* bar gene, allowing for visual selection of fluorescing transformed tissues.

Regeneration of Transformed Cells

Conventional regeneration methods, well known in the art, may be used for corn species. (Duncan et al., 1985; U.S. Pat. Nos. 5,484,956; 5,489,520; 5,177,010; 5,641,664; and 5,350, 689, all incorporated herein by reference.)

Soybean regeneration may be achieved either by the methods of Ranch et al., 1985, or preferably by the methods disclosed herein (Example 9).

EXAMPLES

The present invention is further detailed in the following Examples, which are offered by way of illustration and are not intended to limit the invention in any manner. Standard techniques well known in the art or the technique specifically described below are utilized.

Example 1

Delivery of Molecules into Cells and Tissues by the Method of the Invention

Aerosol droplets containing nucleic acids and/or proteins were introduced into target tissue such as cells using the aerosol beam apparatus of the invention (FIG. 1). The aerosol was produced by a microflow nebulizer such as the HEN from J. E. Meinhard Associates Inc., or the MCN100 style M4 nebulizer from Cetac Technologies Inc. (Liu and Montaser, 1994; Tan, et al., 1992). The nebulizing gas was high purity compressed-helium which was regulated with an ACCU-TROL gas regulator—876X model RS-7-4 and filtered through an Arrow F300-02 IT filter. When HEN and the MCN100 microflow nebulizers were used, the nebulizing pressure was preferably 20-30 psi but worked within the range from about 10 psi to about 40 psi. The entrainment gas filled the entrainment tube and entrained the aerosol droplets in a straight line. Unfiltered, high purity compressed helium was used as the entrainment gas and was regulated by an Arrow R262 regulator to produce slight positive pressure as measured by a Gilmont model 65 mm gauge. The entrainment housing contained a nucleospot to reduce electrostatic charges and was maintained at a temperature of about 42° C. to about 55° C., and most preferably about 55° C. This reduced coalescing of the aerosol droplets and was controlled by two Omega CN9000 series temperature controllers. The sample flow rate to the nebulizer was controlled by a Harvard 11 infusion only syringe pump. The flow rate was 1 to 1200 µl/min using a sterile Becton Dickinson 1 cc plastic syringe with a 0.2 micron filter attached. The sample contained 10 mM Tris buffer (pH 7.0) or a carbohydrate molecule (for example 1 g/l sucrose) and the molecules to be delivered.

As discussed previously, venting of excess aerosol which is reported in U.S. Pat. No. 5,240,842 is not necessary with the method of the invention. Unexpectedly, venting drastically reduced effectiveness of the method of the invention. The target tissue was placed on solidified agar medium in a petri dish on the stage, about 3 cm below the nozzle tip. The stage was mounted on a XY-4040 precision grade table (New England Affiliated Technologies) which was controlled by LabVIEW 5.0 software (National Instruments). The stage moved in a straight line at the rate of 20-80 mm/sec with about 0.3 mm to 1.0 mm distance between passes. Typically a run of 1.0-3.0 minutes was performed which covered about a 2.0 to 4.0 cm diameter area of target tissue. The chamber vacuum was maintained at around 26 to about 30 inches Hg throughout a given run by a Welch 1405 DuoSeal vacuum pump. The vacuum created a pressure differential that was mediated through the nozzle. When the aerosol droplets produced by the nebulizer in the chamber of comparably high pressure passed through the nozzle, they greatly accelerated into the vacuum of the lower chamber. A small beaker of water was placed in the vacuum chamber to prevent loss of moisture from the target tissue. The nozzle was preferably a luer-lock 24 gauge (305 um inside diameter) Becton Dickinson syringe needle cut off just proximal to the plastic holder. However, syringe diameters of about 200 to about 500 microns as well as nozzles known in the art, other than syringes, can be used.

Parameters will vary for particular plant tissues. Tissue which can withstand the damage caused by the beam may produce more transformants when subjected to a more intense barrage of aerosol droplets (produced by using a wider orifice, by slowing stage speed, or by decreasing the distance between passes, for example).

Briefly, the treatment of target tissue with the aerosol beam apparatus was performed as follows: 1) place petri dish with tissue on the stage and close vacuum chamber; 2) start the vacuum pump; 3) start the syringe pump; 4) set the nebulizing gas pressure; 5) set the entrainment gas pressure, and by this time the correct vacuum in the chamber is reached; and 6) start the movement of the stage and let the system run for the time needed to complete the run. After the run is completed, shut down the stage, vacuum, syringe pump, nebulizing gas, entrainment gas, and remove target tissue from the chamber.

Example 2

Introduction of Nucleic Acid into Corn Callus and Detection of Transient Expression Embryogenic corn callus of Stine inbred 963 was transferred from stock culture maintenance medium, DN62 (Table 1) to a medium formulated to provide osmotic stress to the tissue. A preferred embodiment of the invention, DN62OSM medium was used (Table 1). Preferably the embryogenic callus was transferred two to three days after transfer to fresh maintenance medium, a time when the cells are dividing rapidly (for maintenance, cultures are routinely transferred every ten days). After at least 45 minutes (preferably an hour) and up to 24 hours on this medium, tissue was collected and oriented in the center of the target surface prior to beaming. After beaming, the tissue was allowed to incubate on DN62OSM medium for one day.

The plasmid used in transient expression experiments was preferably PBARGUS which was obtained from the Plant Gene Expression Center, Albany, Calif., although other plasmids known in the art can be used. Plasmid BARGUS contains a beta-glucuronidase (GUS) expression cassette consisting of a GUS gene driven by the corn adh1 promoter and adh1 intron1 terminated with a nos terminator, and a bar expression cassette consisting of a bar gene driven by a CaMV 35S promoter and an adh1 intron terminated with a nos terminator. The GUS expression cassette is used to detect transient expression while the bar expression cassette confers tolerance to the herbicide bialaphos. Thus, if desired, selection of stably transformed clones could be achieved. Another plasmid used in transient assays was p350096, which has the CaMV 35S promoter, alcohol dehydrogenase intron six (IV6) driving the GUS gene which is terminated with the nopaline synthase (nos) 3' end. Approximately two micrograms of supercoiled plasmid DNA was added to 1.0 ml of the buffered solution, however, higher and lower concentrations of DNA can be used. For example, DNA concentrations as high as about 20 µg/ml of DNA and as low as about 0.1 µg/ml to about 1.0 µg/ml were effective, although delivery was less effective when using 0.1 µg/ml. In terms of number of DNA molecules, there are approximately 99 billion molecules in 1 ug of pBARGUS DNA. A DNA concentration of 0.1 ug/ml produced less transient expression than did 2.0 ug/ml while a DNA concentration of 1.0 ug/ml produced similar transient expression to 2.0 ug. Higher concentrations than 2.0 ug produced marginally more intense transient expression. Supercoiled or linear DNA could be used in transient expression experiments, however, in this example supercoiled was preferred because of the ease of preparation. Plasmid DNA was isolated using Qiagen midi or maxi preps as described by the manufacturer.

The aerosol beam procedure used to transform corn callus was essentially as previously described (Example 1). Preferred parameters included an entrainment tube or housing maintained at about 55° C. with the sample solution flow rate set at about 0.5 ml/hour to about 1.0 ml/hour (8 µl/min. to about 17 µl/min.) and the vacuum chamber pressure maintained at about 29 inches Hg. Treatment of target tissue with the aerosol beam typically continued for about one to about three minutes, however, beaming can continue for as long as the target tissue can survive being held in a vacuum which, in the case of immature corn embryos and embryogenic callus, is at least 3 minutes.

Sterile technique was used routinely to prevent contamination of target tissue. A seventy percent ethanol solution was sprayed on the inside of the vacuum chamber and entrainment tube prior to the start of an experiment and the tubing attached to the nebulizer and the microflow nebulizer itself were rinsed out with 70% ethanol which was followed by a wash with sterile water before adding the sample solution. Sterile water was replaced with the sample solution before treating the target tissue with the aerosol beam apparatus.

Approximately one day after treating the corn callus with the aerosol beam apparatus, transient expression was evaluated by histochemical analysis. Embryogenic callus was incubated in the presence of the substrate X-gluc (Gold Biotechnology, Inc.) at a concentration of 0.5 mg/ml in 0.1 M sodium phosphate buffer pH 7.0 and 0.1% Triton-x-100 at 37° C. After 1-4 hours blue spots appeared indicating GUS expression which verifies that the GUS expression cassette was introduced into the cell with the aerosol beam apparatus. Transient expression results were used to compare the efficiency of DNA delivery, using equivalent amounts of DNA, to embryogenic callus using either the method of the invention or a DuPont PDS 1000 particle delivery device. Delivery using the method of the invention was readily observed to be more efficient in terms of the number of color forming units, their size and the intensity of their color.

TABLE 1

Medium for Pretreatment, Beaming and Selection

| Ingredients in 1 liter | DN62 | DN62AG | DN62AB | DN62OSM |
|---|---|---|---|---|
| N6 salts | 3.98 g | 3.98 g | 3.98 g | 3.98 g |
| N6 vitamins | 1 ml | 1 ml | 1 ml | 1 ml |
| Asparagine | 800 mg | 800 mg | 800 mg | 800 mg |
| Myo-inositol | 100 mg | 100 mg | 100 mg | 100 mg |
| Proline | 1400 mg | 1400 mg | 1400 mg | 1400 mg |
| Casamino acids | 100 mg | 100 mg | 100 mg | 100 mg |
| 2,4_D | 1 mg | 1 mg | 1 mg | 1 mg |
| Sucrose | 20 g | 20 g | 20 g | 20 g |
| Glucose | | 10 g | | |
| Sorbitol | | | | 45.5 g |
| Mannitol | | | | 45.5 g |
| AgNO$_3$ | | 10 mg | 10 mg | |
| Bialaphos | | | 1 mg | |
| Gelrite | 3 g | 3 g | 3 g | 3 g |
| pH | 5.8 | 5.8 | 5.8 | 5.8 |

DN62B—as for DN62 with the addition of 1 mg/l bialaphos
DN62AGB—as for DN62AG with the addition of 1 mg/l bialaphos.
N6 salts—Sigma Plant Culture Catalogue ref. C1416
N6 vitamins: 2 mg/l glycine, 0.5 mg/l nicotinic acid, 0.5 mg/l pyridoxine HCl, 1 mg/l thiamine HCl (after Chu C.C. (1978)). The N6 medium and its application to anther culture of cereal crops. In: Proc. Symp. on Plant Tissue Culture. Sci. Press, Beijing, pp. 43–50.

Example 3

Introduction of Nucleic Acid into Immature Corn Embryos and Detection of Transient Expression Immature embryos of Stine inbred 963 (10 days' post-pollination) were also used for transient expression experiments. In this case embryos were dissected out at between 1 mm and 2 mm in length and either used immediately or maintained for up to 10 days, preferably 2 to 3 days, on DN62AG medium (Table 1) prior to beaming. Forty-five minutes before beaming the embryos were transferred to DN62OSM. After beaming as described in Example 2 for callus tissue, the embryos were allowed to remain on DN62OSM for 30 minutes before final transfer to DN62AG for one day.

One day after treating immature embryos with the aerosol beam apparatus transient expression was evaluated by histochemical analysis. Immature embryos were incubated in the presence of the substrate X-gluc (Gold Biotechnology) at a concentration of 0.5 mg/ml in 0.1 M sodium phosphate buffer pH 7.0 and 0.1% Triton-x-100 at 37° C. After 1-4 hours blue spots appeared indicating GUS expression which verifies that the GUS expression cassette was introduced into the cell with the aerosol beam apparatus. Transient expression results obtained using a DuPont PDS 1000 particle delivery device were compared with those obtained using the method of the invention. Equivalent amounts of DNA were used. Blue spots appeared more rapidly, were more numerous, larger and more intense using the method of the invention.

Example 4

Introduction of Nucleic Acid into Corn Callus and Detection of Stable Transformation The plasmids used for stable transformation preferably contained the bar expression cassette from PBARGUS, as described previously. This cassette allowed for selection of a stable transformants using the herbicide bialaphos. Plasmid pRBTBAR contained a Bt expression cassette along with the bar expression cassette from pBARGUS. Plasmid pBARGFP contained the bar expression cassette along with a gfp expression cassette. In the case of this plasmid the bar expression cassette was from pSLJ2011 which was obtained from The Sainsbury Laboratory, England. The bar gene was driven by the CaMV 35S promoter, TMV omega enhancer, and terminated by the octopine synthase terminator (ocs). The gfp (EGFP) gene was obtained from Clonetech, Inc., and was driven by a CaMV 35S promoter and terminated with a CaMV 35S terminator. For stable transformation experiments, the DNA concentration varied from 2 ug/ml to 20 ug/ml and the DNA was either supercoiled or linear. The supercoiled DNA was isolated as previously described (Example 2). The linear bar expression cassette was isolated by digesting 20 ug of pBARGUS with HindIII as described by the manufacturer Promega, separated on a 1% agarose gel as is common in the art and extracted from the agarose gel using Qiaex II as described by the manufacturer (Qiagen). Usually 50% of the DNA found in a band was recovered which would have been the equivalent in moles to 10 ug pBARGUS.

Embryogenic callus, maintained on DN62, is transferred off DN62 1 to 10 days, preferably 3 to 6 days, after the previous transfer and placed on DN62OSM for 45 minutes prior to beaming. After beaming as described in Example 1, callus was allowed to remain on this medium for 30 minutes. The beamed tissue was then transferred to DN62B (see Table 1) for selection. Various selection schemes were tested and were successful including selection on bialaphos at concentrations of up to 10 mg/l. Success in selection was enhanced by the use of the gfp gene in combination with the bar gene, allowing for visual selection of fluorescing transformed tissues.

Example 5

Regeneration of Stably Transformed Corn Callus

A preferred pathway used to produce stably transformed plants from beamed embryogenic callus (Stine 963) was performed as follows: after beaming on DN62OSM, the callus was transferred to DN62B and cultured for a passage of 14 days; after this period it was transferred again to further passages of fresh DN62B medium; after between three and six passages on DN62B clones were identified by growth in the presence of bialaphos (Table 1).

Clones were induced to regenerate plants by selecting actively growing Type II callus from clonal tissue, with the objective of obtaining a high frequency of so-called "water tower" embryo structures (U.S. Ser. No. 09/203,679 incorporated herein). This type of tissue is preferred because regeneration of whole plants is improved. These tissues were then transferred to DNROB (Table 2). On this medium embryo maturation occurs. Maturing tissues were then transferred off DNROB after two to three weeks either to a fresh plate of DNROB or to 0.1 NABA6S (Table 2). After a further one to two weeks, embryos with a shoot meristem were placed on MSOG medium (Table 2) or ½MSIBA (Table 2), where germination occurs. Plantlets were then transferred to tubes containing ½MSIBA medium for promotion of further root and shoot development prior to final transfer to soil.

TABLE 2

Media for Regeneration

| Ingredients in 1 liter | DNROB | 0.1NABA6S | MSOG | ½MSIBA |
|---|---|---|---|---|
| MS Salts | 4.43 g | 4.43 g | 4.43 g | 2.215 g |
| Asparagine | 800 mg | | | |
| Proline | 1400 mg | | | |
| Na2EDTA | 37.3 mg | 37.3 mg | 37.3 mg | 37.3 mg |
| Casamino acids | 100 mg | | | |
| Nicotinic Acid | 0.5 mg | | | |
| 1-naphthaleneacetic acid | | 0.1 mg | | |
| Abscisic acid | | 0.1 mg | | |
| Gibberellic Acid | | | 0.1 mg | |
| Indole 3 Butyric Acid | | | | 0.1 mg |
| Sucrose | | 60 g | 30 g | 20 g |
| Sorbitol | 20 g | | | |
| Bialaphos | 1 mg | | | |
| Gelrite | 2 g | | | |
| Phytagar | | 7 g | 7 g | 7 g |
| pH | 5.8 | 5.8 | 5.8 | 5.8 |

The presence of an expressing bar gene was confirmed in the regenerants by leaf painting with Liberty. Mendelian ratios of an expressing bar gene were routinely observed in the progeny of the regenerants (Table 3).

TABLE 3

| | Target Tissue | Liberty Resistant | Liberty Sensitive | Ratio |
|---|---|---|---|---|
| Regenerant* 2-Event B1 | Callus | 77 | 23 | 3:1 |
| Regenerant 8-Event B2 | Embryo | 60 | 18 | 3:1 |
| Regenerant 2-Event B3 | Embryo | 74 | 25 | 3:1 |
| Regenerant 1-Event B5 | Callus | 71 | 26 | 3:1 |
| Regenerant 7-Event B6 | Callus | 58 | 41 | 1.4:1 |

*Regenerant number refers to the number of the plant regenerated from the indicated "Event".

Example 6

Introduction of Nucleic Acid into Immature Corn Embryos and Detection of Stable Transformation Immature embryos of Stine 963 were excised from kernels usually around 10 days' post-pollination. At this time the embryos were around 1.0 to 1.5 mm in length. Embryos were then placed on DN62AG medium for two to three days. After this time they were then placed on DN62OSM for 45 minutes prior to beaming. After beaming as described in Example 1, the embryos remained on DN62OSM for 30 minutes and then were transferred either to DN62AG for five days prior to transfer to DN62AGB, or to DN62AGB directly (Table 1).

Example 7

Regeneration of Stably Transformed Corn Embryos

After a further week's culture the corn embryos from Example 6 were then transferred to DN62AB (Table 1). After several 14-day passages on DN62AB, clones can then be selected. Clonal tissue was induced to regenerate plants according to the description in Example 5.

In one experiment 44 immature embryos were beamed and 5 clones were recovered (11.3%) which gave rise to transformed plants. The presence of an expressing bar gene was confirmed in these clones as described in Example 4.

Segregation of expression of the bar gene in Stine elite inbred 963 after transformation using the method of the invention is shown in Table 3. All regenerants were selfed. Heritability of the nucleic acid inserted by the method of the intention was reflected in the expected ratios for inheritance of a single dominant gene in the progeny of transformed plants. The fertility of the transgenic plants produced using the method of the invention is comparable to that of nontransformed regenerated plants of the same inbred.

Transformation frequency using immature embryos of Stine elite inbred 963 and the DuPont PDS-1000 particle gun was around 1% (after bombardment of several thousand embryos). With the method of the present invention, success rates of up to 20% were noted with an average of around 3% over all experiments.

Example 8

Improved Growth Rate of Soybean Embryogenic Callus

In another embodiment of the present invention, a novel culture media may be used to stimulate high frequency production of embryogenic soybean callus. Improvement varied with the genotype being cultured. The length of time required for a culture passage was unexpectedly reduced to two weeks with the use of this novel medium as compared to four weeks typical with other media. The inclusion of one or more of four media constituents, coconut water, myoinositol, phytic acid and inorganic phosphate concentration, enhanced embryogenic callus production and allowed significant improvements to be made to transgenic clone production in terms of number of clones recovered, embryo morphology, and reduction in the time needed to identify the clones and regenerate plants from them. The medium of Ranch et al., 1985 (referred to herein as B1-30) was used as the basal medium. An example of the medium of the present invention is B1-30 3Co5My0.25PA0.5K (footnote, Table 5). Although this medium is a preferred emobodiment of growth medium, other conventional media may be utilized in the practice of the invention.

Coconut water has been included in tissue culture media for over 50 years. Coconut water is liquid taken from coconuts to promote growth in plant tissue cultures. It is deproteinized then filter-sterilized. An example is Sigma Biosciences' Cat. No. C5915. The beneficial effects of coconut water were first noted by Overbeek et al., 1941, when it was found to permit the growth in culture of heart-stage *Datura* embryos. In subsequent years, Steward and others showed that coconut water was capable of stimulating responses from a variety of plant tissues (Steward et al., 1969). Most commonly coconut water is used at concentrations of between 5% and 10% by volume of the final culture medium. The role of coconut water in stimulating the growth of embryogenic callus in soybean was investigated and it was discovered that its effect on cotyledon explants routinely used to initiate embryogenic callus of soybean was detrimental when tested at these concentrations. No embryogenic callus was produced in these experiments. However, when coconut water was added to media used for the maintenance of embryogenic callus, an unexpected beneficial effect was noted in terms of rate of growth and quality of somatic embryo morphology. In view of this result, coconut water was routinely included in media for the maintenance of embryogenic callus at concentrations of between 3% and 6% by volume of the final culture medium.

One key component of coconut water is myoinositol (Pollard et al., 1961). In an attempt to improve the growth of embryogenic soybean callus with components of coconut water, it was discovered that myoinositol was effective in this regard. Myoinositol has been included in tissue culture media for a variety of plant species. Although apparently not required for all species (Halperin, 1966), it is routinely included in media such as the widely used Murashige and Skoog formulation (Murashige and Skoog, 1962) at a concentration of 100 mg/l. It is at this concentration that it has been included in media used for the culture of embryogenic callus of soybean (e.g., see Ranch et al., 1985). Unexpected results revealed a pronounced and beneficial effect of myoinositol when used at much higher concentrations (up to 10 g/l) alone or in combination with coconut water.

There are no known reports of the inclusion of phytic acid in culture media for any plant species. Soybean seeds are rich in natural chelating agents, the most prominent of which is phytic acid (Gibson and Ullah, 1990). Substantial amounts of phosphate are stored in seeds in the form of phytate (Raboy, 1990). It is possible that the capacity of phytic acid to sequester inorganic phosphate has a significant impact upon C partitioning into either starch or sucrose. At 1 gm/l in B1-30, embryogenic callus of a range of genotypes exuded starch, possibly confirming the impact of phytic acid on C partitioning. Surprisingly, after this initial effect the soybean callus grew very vigorously and produced many small globular embryos. Further experiments indicated that phytic acid at 1, 5, 10, 50, 100, 250, 500 and 1000 mg/l in B1-30 significantly increased the rate of growth of embryogenic callus during the initial culture passage and/or during maintenance as a stock culture. At 3000 mg/l a clear detrimental effect was observed and embryogenic callus browned and died. Best results over many passages were obtained with the addition of about 5 mg/l to about 250 mg/l phytic acid to the culture medium depending on the genotype.

Inorganic phosphorous in the form of $KH_2PO_4$, in excess of the amount conventionally used, was added to the base medium (B1-30) along with myoinositol and coconut water. This medium was tested against B1-30 supplemented with phytic acid in addition to $KH_2PO_4$, myoinositol and coconut water. Beneficial effects were noted with 500 and 1000 mg/l both with and without phytic acid.

TABLE 4

| Ingredients in 1 Liter | Growth Media for Soybean* | | |
|---|---|---|---|
| | B1-30 | B3 | B5G |
| Ms Salts | 4.43 g | 4.43 g | |
| B5 Salts | | | 3.19 g |
| NaEDTA | 37.3 mg | 37.3 mg | 37.3 mg |
| 2,4-D | 30 mg | | |
| Activated Charcoal | | 5 g | |
| Phytagar | 8 g | 8 g | |
| Gelrite | | | 2 g |
| pH | 5.8 | 5.8 | 5.8 |

*Variations of media referred to in Table 4 were tested, e.g., B1-30 3Co5My, which was made made by adding 3% coconut water and 5 gm/l myoinositol to B1-30. Other variations included: B1-30 3Co5My0.25 PA0.5K which contained B1-30 basal medium plus 3% coconut water, 5 gm/l myoinositol, 0.25 gm/l phytic acid, and 0.5 gm/l additional $KH_2PO_4$ and ½ B5G which contained all ingredients of B5G medium at half strength.

Using the improvements described above, new and effective media were developed for the production of embryogenic soybean callus from a variety of elite genotypes. (See Example 9). The media of the present invention are effective for a range of germplasm and also greatly reduce the time required to obtain embryogenic callus in sufficient quantity for transformation experiments.

Example 9

Culture of Soybean Callus

To initiate cultures, pods were surface sterilized and embryos with immature cotyledons 3 to 4 mm in length were excised. Individual cotyledons were then cultured on B1-30 medium (Table 4) or on B1-30 media containing 100 to 1000 mg/l phytic acid. Typically, a small amount of embryogenic callus proliferated from some of these cotyledon explants. This callus was then excised and transferred to a B1-30 medium containing between 3% and 6% coconut water or/and between 1 g/l and 10 g/l myoinositol. The coconut water and myoinositol requirements for optimum sustained embryogenic callus growth were found to vary according to genotype. Exemplary results using a range of concentrations of these components are summarized in Table 5.

TABLE 5

Comparative Growth Response

| Stine Genotype | Media | Response |
| --- | --- | --- |
| 96E750 | B1-30 3Co 10My | best |
| 96E750 | B1-30 3Co 5My | good |
| 96E750 | B1-30 3Co | good |
| 96E750 | B1-30 | worst |
| 96E692 | B1-30 3Co 5My | best |
| 96E692 | B1-30 6Co 5My | v. good |
| 96E692 | B1-30 3Co 3My | v. good |
| 96E692 | B1-30 3Co 1My | good |
| 96E692 | B1-30 3Co | good |
| 96E692 | B1-30 3Co 10My | fair |
| 96E692 | B1-30 | worst |
| 98CB371 | B1-30 3Co 10My | best |
| 98CB371 | B1-30 3Co 5My | good |
| 98CB371 | B1-30 | worst |
| 98CB166 | B1-30 3Co 10My | best |
| 98CB166 | B1-30 3Co 5My | good |
| 98CB166 | B1-30 | worst |

In other experiments it was unexpectedly discovered that further enhancement of embryogenic callus formation was possible by addition of about 1 to about 1000 mg/l of phytic acid and/or additional inorganic phosphate in the form of $KH_2PO_4$ to B1-30 with myoinositol and coconut water. The amounts required for improvement vary with genotype. With these two additional constituents, suitable amounts of embryogenic callus for transformation experiments can be obtained within three to six months, a significant improvement over the year or 18 months typically required for elite genotypes on standard media, such as B1-30.

Also effective in preparing tissue for beaming is a brief exposure to coconut water, myoinositol and about 1 gm/l phytic acid for from about 3 to 10 days immediately before beaming. Embryogenic callus taken off this medium and beamed directly grows vigorously after beaming in the period before exposure to a selection agent such as bialaphos (Example 11) allowing for greater survival and growth of transformed cells. This improved survival increases the chances of clone identification during selection.

Example 10

Introduction of Nucleic Acid into Soybean Callus and Detection of Transient Expression The apparatus, parameters and beaming method used to introduce nucleic acid into soybean callus were essentially as described in Example 1, unless otherwise indicated in this Example. The sample solution containing DNA was prepared as previously described (Example 2).

Embryogenic soybean callus of Stine 13404-TT was transferred after a culture passage of about 28 to 30 days from stock culture medium (B1-30 3Co5My 50 mg/l phytic acid—Table 4) to the center of a target plate containing the same medium. Embryogenic soybean callus can survive being held in a vacuum for at least 10 minutes. After one to three days' growth on the target plate, the soybean embryogenic callus is exposed to an aerosol beam of pSLJ4K1 (the 35 S promoter driving the gus gene). After beaming the tissue is spread out on a fresh plate (to minimize the risk of contamination) of the same medium.

Approximately one day after treating the soybean callus with the aerosol beam apparatus, transient expression was evaluated by histochemical analysis. Embryogenic callus was incubated in the presence of the substrate X-gluc (Gold Biotechnology, Inc.) at a concentration of 0.5 mg/ml in 0.1 M sodium phosphate buffer pH 7.0 and 0.1% Triton-x-100 at 37° C. After 1-4 hours blue spots appeared indicating GUS expression which verifies that the GUS expression cassette was introduced into the cell with the aerosol beam apparatus. Transient expression results were used to compare the efficiency of DNA delivery, using equivalent amounts of DNA, to embryogenic callus using either the method of the invention or a DuPont PDS 1000 particle delivery device. Delivery using the method of the invention was readily observed to be more efficient both in terms of the number of color forming units and the intensity of their color.

Example 11

Introduction of Nucleic Acid into Soybean Embryogenic Callus and Detection of Stable Transformation The plasmids used to stably transform soybean were pSB12BARAHAS and pNPTAHAS. Plasmid SB12BARAHAS contained the bar expression cassette from pSLJ2011 which consisted of a CaMV 35S promoter, TMV omega enhancer, bar gene, and nos terminator. Plasmid SLJ2011 was obtained from The Sainsbury Laboratory at The John Innes Center, England. The bar expression cassette was combined with a genomic fragment from *Arabidopsis* harboring a mutant ahas gene (American Cyanamid). Plasmid pNPTAHAS contained an npt (neomycin phosphotransferase) expression cassette consisting of a CaMV 35S promoter, TMV omega enhancer, npt gene, and ocs terminator, and the same ahas expression cassette described above. The npt expression cassette was from plasmid SLJ481 (Sainsbury Laboratory, John Innes Center, England). The npt expression cassette provides tolerance to the antibiotic kanamycin and the bar expression cassette provides tolerance to the herbicide bialaphos. For purposes of example, supercoiled DNA was used, however, linear DNA or nucleic acid can be expected to work equally well. DNA concentration varied from 2 ug/ml to 20 ug/ml. For pSB12BARAHAS approximately 64 billion molecules of DNA were delivered per 1 ug.

Embryogenic calluses of several Stine elite varieties, including 96E750, 96E94, 97E986, 96E144 and 96E692, were separately collected into the center of plates of B1-30 3Co5My or B1-30 3Co5My0.25PA0.5K (Table 4) three days after transfer to fresh medium. The tissue was then beamed with one of the plasmids described above. After beaming (as described in Example 10) the embryogenic callus was transferred to fresh B1-30 3Co5My or B1-30 3Co5My0.25PA0.5K for one passage of a month. The tissue was then transferred to selective medium containing either 300 mg/l kanamycin or 1 mg/l bialaphos depending on the plasmid used. With bialaphos, selection typically was maintained at 1 mg/l for the first two one-month passages and then increased to 2 mg/l for the following three to seven months. On both bialaphos and kanamycin clones were identified after between five and nine transfers on selective medium. Clones were identified when tissue generated by transformation experiments began to grow vigorously on medium containing a selective agent. Once identified, clonal tissue was allowed to increase and was then regenerated into plants according to the following protocol: (1) Embryogenic structures were transferred off B1-30 3Co5My or B1-30 3Co5My0.25PA0.5K to B3 medium (Table 4); (2) after 3 to 4 weeks' growth on this medium clusters of maturing embryos were separated out into individual structures and either maintained on the same plate or transferred to fresh medium; (3) after another 3 to 4 weeks maturing embryos were transferred to B5G medium (Table 4) containing activated charcoal and placed in the light; (4) embryos which then elongated and produced roots were transferred to tubes containing ½ B5G medium (Table 4) with no activated charcoal where they continued development into plantlets; and (5) these plantlets were removed from the tubes and placed into pots.

Transformation frequency with embryogenic callus of elite Stine soybean lines was greater using the method of the invention than that achieved in similar experiments using the Dupont particle gun. This result was consistent with the results obtained for transient expression in embryogenic soybean callus where grater delivery of DNA was observed using the method of the invention when compared to the Dupont gun. The presence of an expressing bar gene or an expressing ahas gene was confirmed by leaf painting (bar) or spraying (ahas). Mendelian ratios of the expressing genes were routinely observed in the progeny of the regenerants.

Example 12

Transformation of Bacteria

Transformation of bacteria using the method of the invention was accomplished as follows: competent *E. coli* DH5 alpha (Gibco BRL) or HB101 cells were thawed on ice and 5 to 50 microliters were combined with 0.2 ml LB broth. The mixture was pipetted to the center of a plate of LB agar (1.5%) containing 100 mg/l ampicillin and allowed to dry. Aerosol beam parameters were the same as those described previously (Example 1) except as noted in this Example. A pUC-derived plasmid encoding for resistance to the antibiotic ampicillin was delivered to the bacterial cells, as is known in the art. The concentration of DNA ranged from about 1.0 to 1000 μg/ml in 10 mM Tris (pH7.0) or a carbohydrate molecule, such as 1 g/l sucrose. The nebulizing pressure was from about 10 to about 40 psi, preferably 30 to 40 psi. The entrainment temperature was maintained in a given experiment and ranged between experiments from about 24° to about 55° C., and was preferably maintained at about 42° to about 55° C. and most preferably at about 55° C. Various sample flow rates were tested ranging from about 0.25 ml/hour to about 2.0 ml/hour (about 4 μl/min. to about 33 μl/min.). Preferably the flow rate was about 8.0 μl/minute to about 17.0 μl/minute.

The stage on which the bacterial cells were placed was located at a distance of from about 1.5 cm to about 5.0 cm from the end of the nozzle with a preferred distance of between about 1.5 cm and about 3.2 cm. The speed at which the stage moved during beaming was adjusted to about 10 mm/sec to about 100 mm/sec with a preferred speed of about 20 mm/sec to about 100 mm/sec. The distance between passes was varied from about 0.2 mm to about 1.0 mm. Most preferable distance between passes was about 0.3 mm to about 0.4 mm.

The vacuum in the sample chamber was varied from about 26 psi to about 30 psi with best results obtained at the higher vacuum pressures, for example 29 psi. Nozzles with orifices of about 254 to 500 microns were used. Preferable were nozzles with diameters of about 300 to about 330 microns.

After beaming, plates were incubated at 37° C. for 15 to 20 hours. No growth was observed in the control without DNA, however, when DNA was introduced, growth of thousands of transformed colonies was evident. As a control, the same sample of DNA which was beamed was sprayed on the cells using the same microflow nebulizer used with the aerosol beam apparatus but with no supersonic acceleration of aerosol droplets. No transformed colonies resulted from this treatment. As an additional control, bacteria were bombarded with tungsten particles coated with the same pUC-derived plasmid using the particle gun and a protocol essentially as described by Smith et al. (1992). This protocol produced no transformants. The protocol of Smith et al. (1992), was altered in the practice of the present invention in that the relative humidity was not adjusted nor was osmoticum used.

Example 13

Use of the Method of the Invention to Increase Transformation Frequency

Transformation frequency in plants can be increased by introducing restriction enzymes simultaneously with the transforming DNA using the method of the present invention. Parameters for the aerosol beam apparatus are as described previously for plant cells (Example 1). Corn and soybean target tissue are prepared as described previously (Examples 4 and 5). For selection of transformants, a number of different selective agents can be used including, but not limited to, bialaphos, kanamycin, hygromycin, and imazapyr. By way of illustration, selection using imazapyr and mutant AHAS genes is described.

Plasmid pCD220 carries a mutant corn AHAS gene. Expression of this gene in corn confers resistance to the herbicide Arsenal (active ingredient imazapyr) manufactured by American Cyanimid. The plasmid is digested with the restriction enzyme Xba I as described by Promega. The linearized DNA fragment carrying the gene and regulatory elements necessary for expression in corn are separated from the remaining plasmid DNA in a 1% agarose gel as practiced in the art. The genomic DNA is then purified from the gel using the QIAEX II gel extraction kit according to the manufacture (Qiagen). About 10 micrograms of linear DNA with Xba I compatible ends and 200 units of Xba enzyme are combined in 1 ml of 10 mM Tris pH 7.0, or in 1 ml of a buffer solution recommended for Xba I by the manufacturer (Promega). The solution containing the DNA and the enzyme is then beamed into corn cells as previously described. Transformants are selected as described previously. The simultaneous introduction of DNA with the appropriate restriction enzyme can significantly increase the frequency of transformation.

A mutant AHAS gene from *Arabidopsis* can be introduced into soybean cells using the same methods. Plasmid AC321 is digested with Xba I as described above for plasmid pCD220. This *Arabidopsis* genomic fragment is then used for transformation of soybean together with the Xba I restriction enzyme. Again, the number of transformants obtained using the enzyme together with the DNA can be significantly higher than when using the DNA alone.

Example 14

Introduction of Carbohydrate and Plant Growth Regulator into Cells

Glucose and 2,4-D were introduced into cells of cultured immature embryos of Stine corn inbred 963 by the method of the present invention. Preparation of embryos and parameters for the aerosol beam apparatus were the same as described for Example 6. Glucose was used at a concentration of 1 gm/l. 2,4-D was used at a concentration of 0.1 mg/l. After beaming with pBARGUS, glucose, and 2,4-D, stably transformed clonal tissue was selected and plants regenerated as described in Example 7. A significant increase (2 to 10 fold) in the number of clones recovered was noted from embryos beamed with glucose, 2,4-D and DNA when compared with embryos beamed with DNA alone. Similar results were obtained using 1 g/l sucrose in place of 1 g/l glucose.

Example 15

Introduction of Protein into Cells

The protein glucuronidase was introduced into embryogenic callus cells of Stine corn inbred 963 by the method of the present invention. Target preparation and aerosol beam parameters were as described in Example 2. Glucuronidase from Sigma (cat # G2035) was used at a concentration of 320 µg/ml in 10 mM Tris (pH 7.0). After treating of corn callus with the aerosol beam apparatus, the tissue was immediately incubated in X-gluc substrate, as described in Example 2. After 1 to 4 hours blue spots appeared indicating the intracellular presence of GUS. The intracellular presence of GUS was then confirmed by microscopic examination. As a control, protein was applied to the surface of the embryogenic callus with an atomizer and the callus was then incubated for about 1 to 4 hours in x-gluc substrate. No blue spots were observed with this treatment.

Example 16

Introduction of Nucleic Acid Together with Other Molecules into Cells

Nucleic acid and protein were simultaneously delivered into bacterial cells. Preparation of bacteria and parameters for the aerosol beam apparatus were the same as described previously for delivery of DNA into bacteria (Example 12). The same buffer, plasmid, and plasmid concentration was used as described in the transformation of bacteria. Ribonuclease A (RNASE A) (Sigma cat. no. R6513) was added to the DNA sample at a final concentration of 2.5 µg/ml. After the sample of DNA and RNASE A was beamed into bacteria, no colonies were observed on medium containing ampicillin indicating the cytotoxic effect of RNASE A in the cells.

As a control, RNASE A at the same concentration used for beaming was pipetted on the cells after the cells were beamed with DNA only. Here, transformed colonies grew indicating that the RNASE A was not taken up naturally by the cell. To verify that the RNASE A was not degrading the plasmid, the plasmid treated with RNASE A was run on a standard 1% agarose gel. After staining the DNA with ethidium bromide, the DNA appeared intact and no degradation was evident. As a further control, RNASE A was inactivated with diethylpyrocarbonate (DEP). Inactivation was carried out as follows: 2.5 micrograms of RNASE A was added to 1.0 ml 10 mM Tris (pH 7.0), then 4.0 µl of DEP was added. This mixture was vortexed and incubated for 2-4 hours at room temperature, after which time, gases were evacuated from the tube by heating the mixture to 85° C. for 15 minutes with the cap of the tube off. DNA was then added and the sample beamed into cells. The introduction of DNA and inactivated RNASE A resulted in the normal transformation of bacteria. Thus, the addition of RNASE A to the DNA did not prevent the DNA from entering the cell. From these experiments it follows that both DNA and protein were delivered together into bacterial cells.

Example 17

Optimization of Sample Flow Rate for Bacteria

Transformation of bacteria using the method of the invention was performed as described in Example 12. The sample flow rate was varied from about 1 µl/minute to about 200 µl/minute. Although sucrose was used in this example, other carbohydrates such as glucose can be used in the practice of the invention. The efficiency of DNA delivery is reflected in Table 6 as number of bacterial colonies able to grow on agar containing 100 mg/l ampicillin at the listed sample flow rates.

The preferred sample flow rate for introduction of DNA into bacteria was about 1 µl/minute to about 200 l/minute, a more preferred flow rate was about 4 µl/minute to about 50 µl/minute and the most preferred flow rate was about 8 µl/minute to about 17 µl/minute.

Example 18

Optimization of Sample Flow Rate for Corn

Introduction of DNA into immature corn embryos was performed using the method of the invention as described in Example 3. The sample flow rate was varied from about 1 µl/minute to about 200 µl/minute. Transient expression results were used to compare the efficiency of DNA delivery. Results are reflected in Table 6 as number of blue spots per embryo at the listed sample flow rates. The preferred sample flow rate for introduction of DNA into corn is about 1 µl/minute to 200 µl/minute, a more preferred rate is about 4 µl/minute to about 50 µl/minute and a most preferred rate is about 8 µl/minute to about 50 µl/minute.

Example 19

Optimization of Sample Flow Rate for Soybean

Introduction of DNA into soybean callus was performed using the method of the invention as described in Example 10. The sample flow rates varied from about 1 µl/minute to about 200 µl/minute. Transient expression results were used to compare the efficiency of DNA delivery. Results are reflected in Table 6 as number of blue spots per plate at the listed sample flow rates. The preferred sample flow rate for introduction of nucleic acid into soybean callus was about 1 µl/minute to about 200 µl/minute, with a more preferred rate of about 4 µl/minute to about 50 µl/minute and a most preferred rate of about 8 µl/minute to about 50 µl/minute.

TABLE 6

| | Flow Rate in Microliters Per Minute* | | | | | | | |
|---|---|---|---|---|---|---|---|---|
| | 1.0 | 2.0 | 4.0 | 8.0 | 17.0 | 50.0 | 100.0 | 200.0 |
| Bacteria | 0 | 0 | 24 | 236 | 179 | 91 | 2 | 2 |
| Corn | <1.0 | 1.0 | 4.0 | 7.5 | 9.0 | 8.0 | 1.0 | <1.0 |
| Soybean | 0 | 0 | 139 | 264 | 249 | 211 | 65 | 22 |

*The effect of sample flow rate on the introduction of DNA into bacteria, corn, and soybean was determined as described in Examples 17, 18 and 19 for the transformation of bacteria, corn, and soybean, respectively. The results in Table 6 represent a typical experiment. For bacteria, the efficiency of DNA delivery was determined by the number of transformed bacterial colonies per plate growing on antibiotic containing medium. For corn the efficiency of DNA delivery was determinedby the number of blue spots per embryo, and for soybean the number of blue spots are per plate.

While the invention has been disclosed in this patent application by reference to the details of preferred embodiments of the invention, it is to be understood that the disclosure is intended in an illustrative rather than a limiting sense, as it is contemplated that modifications will readily occur to those skilled in the art, within the spirit of the invention and the scope of appended claims.

LIST OF REFERENCES

Anand, R. (1992) *Techniques for the Analysis of Complex Genomes* (Academic Press).
Ausubel, F. M., et al. (1992). *Current Protocols in Molecular Biology* (J. Wiley and Sons, N.Y.)
Bilang, R., et al. (1998). "Containing excitement over transplastomic plants". *Nature Biotechnology* 16:333-334.
Bonnassie, S., et al. (1990). "Transfer of plasmid DNA to Brevibacterium Lactofermentum by electrotransformation". *Journal of General Microbiology* 136:2107-2112.
Boynton, J. E., et al. (1988). "Chloroplast transformation in Chlamydomonas with high velocity microprojectiles". *Science* 240:1534-1538.
D'Halluin, K., et al. (1992). "Transgenic maize plants by tissue electroporation". *Plant Cell* 4:1495-1505.
Dagher, S. F., et al. (1991). "Phenotypic conversion of TK deficient cells following electroporation of functional TK enzyme". *Exp. Cell Res.* 198:36-42.
Donn, G., et al. (1990). "Stable transformation of maize with a chimeric modified phosphinothricin acetyl transferase gene from Streptomyces viridochromogenes" In: Abstracts VIIth International Congress on Plant Cell and Tissue Culture, IAPTC, A2-38:53.
Duncan, D. R., et al. (1985). "The production of callus capable of plant regeneration from immature embryos of numerous Zea mays genotypes". *Planta* 165:322-332.
Frame, B. R., et al. (1994). "Production of fertile transgenic maize plants by silicon carbide whisker-mediated transformation". *The Plant Journal* 6:941-948.
Fromm, M. B., et al. (1990). "Inheritance and expression of chimeric genes in the progeny of transgenic maize plants". *Bio/Technology* 8:833-839.
Fromm, M. B., et al. (1986). "Stable transformation of maize after gene transfer by electroporation". *Nature* 319:791-793.
Gelvin, et al. (1990). *Plant Molecular Biology Manual* (Eds.).
Gibson, D. M., and Ullah, A. B. J. (1990). "Phytases and their action on phytic acid. In: Inositol metabolism in plants. *Plant Biology*, vol. 9. Eds., D. J. Morre, W. F. Boss and F. A. Loewus, Wiley-Liss, New York, pp. 77-92.
Glover, D. (1985). *DNA Cloning*, I and II (Oxford Press).
Gordon-Kamm, W. J., et al. (1990). "Transformation of Maize Cells and Regeneration of Fertile Transgenic Plants". *The Plant Cell* 2:603-618.
Green, C. E., et al. (1975). "Plant regeneration from tissue cultures of maize". *Crop Science* 15:417-421.
Grierson et al. (1984). *Plant Molecular Biology* (Blackie, Glasgow).
Guthrie, G., and Fink, G. R. (1991). *Guide to Yeast Genetics and Molecular Biology* (Academic Press).
Halperin, W. (1966). Am. J. Bot 53:443-453.
Hanahan, D. (1983). "Studies on transformation of *Escherichiia coli* with plasmids". *Journal of Molecular Biology* 166:557-580.
Hinchee, M. A. W., et al. (1988). "Production of transgenic soybean plants using *Agrobacterium*-mediated DNA transfer." *Bio/Technology*, 6:915-922.
Ishida, Y., et al. (1996). "High efficiency transformation of maize (*Zea mays* L.) mediated by *Agrobacterium tumefaciens*". *Nature Biotechnology* 14:745-750.
Kaeppler, H. F., et al. (1990). "Silicon carbide fiber-mediated DNA delivery into plant cells". *Plant Cell Reports* 9:415-418.
Kindle, K. L., et al. (1991). "Engineering the chloroplast genome: Techniques and capabilities for chloroplast transformation in *Chlamydomonas* reinhardii". Proceeding of the National Academy of Sciences (PNAS) 88:1721-1725.
Klebe, R. J., et al. (1983). "A general method for polyethylene-glycol-induced genetic transformation of bacteria and yeast". *Gene* 25:333-341.
Klein, T. M., et al. (1988(a)). "Transfer of foreign genes into intact maize cells using high velocity microprojectiles". PNAS 85:4305-4309.
Klein, T. M., et al. (1988(b)). "Factors influencing gene delivery into *Zea mays* cells by high velocity microprojectiles". *Bio/Technology* 6:559-563.
Koziel, M. G., et al. (1993). "Field performance of elite transgenic maize plants expressing an insecticidal protein derived from *Bacillus thuringiensis*". *Biotechnology* 11:194-200.
Kuspa, A., and Loomis, W. F. (1992). "Tagging developmental genes in Dictyostelium by restriction enzyme-mediated integration of plasmid DNA". PNAS 89:8803-8807.
Laursen, C. M., et al. (1994). "Production of fertile transgenic maize by electroporation of suspension culture cells". *Plant Molecular Biology* 24:51-61.
Lowe, K., et al. (1995). *Biotechnology* 13:677-682.
Maniatis, et al. (1982). *Molecular Cloning* (Cold Spring Harbor Laboratories, Cold Spring Harbor, N.Y.).
McCabe, D. E., et al. (1988). "Stable transformation of soybean (*Glycine max*) by particle acceleration." *Bio/Technology* 6:923-926.
Minor, H. (1998). "Production: Performance of GMO's vs Traditional varieties, Southern Perspective." In: Proceedings of the 28th Soybean Seed Research Conference, ASTA, Dec. 9-10 (in press).
Murashige, T., and Skoog, F. (1962). "A revised medium for rapid growth and bioassays with tobacco tissue cultures." *Physiol. Plantarum,* 15:473-497.
Neuhaus, G., et al. (1994). "Tissue-specific expression of as-1 in transgenic tobacco". *Plant Cell* 6:827-834.

Neuhaus, G., et al. (1987). "Transgenic rapeseed plants obtained by the microinjection of DNA into microspore-derived embryos". *Theoretical and Applied Genetics* 75:30-36.

Omirulleh, S., et al. (1993). "Activity of a chimeric promoter with the doubled CaMV 35S enhancer element in protoplast-derived cells and transgenic plants in maize". *Plant Mol. Biol.* 21:415-428.

Oplinger, E. S. (1988). "Production: Performance of GMO's vs. Traditional varieties, Northern Perspective." In: Proceedings of the 28th Soybean Seed Research Conference, ASTA, Dec. 9-11 (in press).

Overbeekm J. van, et al. (1941). "Factors in coconut milk essential for growth and development of very young *Datura* embryos." *Science,* 94:350-351.

Paszkowski, J., et al. (1984). "Direct gene transferto plants". *EMBO* 3:2717-2722.

Pollard, J. K., et al. (1961). "Hexitols in coconut milk: Their role in nurture of dividing cells." *Plant Physiol.* 36:492-501.

Ranch, J. P., et al. (1985). "Plant regeneration from embryo-derived tissue cultures of soybeans." *In Vitro* 21:653-658.

Rhodes, C., et al. (1988). "Plant Regeneration from Protoplasts Isolated from Embryogenic Maize Cell Cultures." *Bio/Technology* 6:56-60.

Rhodes, C., et al. (1988). "Genetically transformed maize plants from protoplasts". *Science* 240:204-207.

Russell, J. A., et al. (1992). "Major improvements in biolistic transformation of suspension-cultured tobacco cells". *In Vitro* 28P: 97-105.

Sambrook, et al. (1989). *Molecular Cloning*: A Laboratory Manual, 2nd. Ed. (Cold Spring Harbor Laboratory Press, Cold Spring Harbor, N.Y.).

Sanford, J. C., et al. (1987). "Delivery of substances into cells and tissues using a particle bombardment process". *Journal of Particle Science Technology* 5:27-37.

Sautter, C., et al. (1991). "Micro-targeting: High efficiency gene transfer using a novel approach for the acceleration of micro-projectiles". *Bio/Technology* 9:1080-1085.

Schiestl, R. H., and Petes, T. D. (1991). "Integration of DNA fragments by illegitimate recombination in *Saccharomyces cerevisiae*". *PNAS* 88:7585-7589.

Steward, F. C., et al. (1969). "Growth and morphogenesis in tissue and free cell cultures." *In: Plant Physiology—A Treatise,* Ed. F. C. Steward, Vol. VB: Analysis of growth: responses of cells and tissues in culture, Academic Press, New York and London, pp. 329-376.

Trick, H. N., and Finer, J. J. (1997). "SAAT: sonication-assisted *Agrobacterium*-mediated transformation." *Transgenic Research* 6:329-336.

Wei, Z., and Xu, Z. (1988). "Plant regeneration from protoplasts of soybean (*Glycine max* L.)." *Plant Cell Reports* 7:348-351.

Widholm, J. M. (1995). "Leguminous plants." *In: Transformation of Plants and Soil Microorganisms,* Eds., K. Wang. A. Herrera-Estrella and M. Van Montagu, Cambridge University Press, pp. 101-124.

Wilson, H. M., et al. (1995). "Maize In: Transformation of plants and soil microorganisms". Cambridge University Press, Cambridge.

Patents and Patent Applications:

Zhao, Z. Y., et al., published PCT WO 98/32326 published in 1988.

U.S. Pat. No. 4,743,548
U.S. Pat. No. 5,240,842
U.S. Pat. No. 5,384,253
U.S. Pat. No. 5,472,869
U.S. Pat. No. 5,550,318
U.S. Pat. No. 5,591,616
U.S. Pat. No. 5,877,023

What is claimed is:

1. A method for the introduction of one or more carbohydrates into a plant cell or a bacterial cell, wherein the method comprises:
   (a) preparing a solution containing said carbohydrates;
   (b) supplying said solution for conversion to aerosol droplets which are produced by a microflow nebulizer at a flow rate of between about 1 μl/minute to about 100 μl/minute;
   (c) producing aerosol droplets comprising said carbohydrates;
   (d) accelerating by jet expansion of an inert gas said aerosol droplets toward said cell wherein said cell is in a vacuum;
   (e) impacting said cell with said accelerated aerosol droplets; and
   (f) producing a cell containing said carbohydrates.

2. The method of claim 1, wherein said cell is a bacterial cell.

3. The method of claim 1, wherein said plant cell is a monocotyledonous plant cell.

4. The method of claim 3, wherein said monocotyledonous plant cell is a corn cell.

5. The method of claim 1, wherein said plant cell is a dicotyledonous plant cell.

6. The method of claim 5, wherein said dicotyledonous cell is a soybean cell.

7. The method of claim 1, wherein said aerosol droplets are continuously targeted toward said cell.

8. The method of claim 1, further comprising the placement of said cell on a target surface the linear and rotational movement of which can be separately controlled.

9. The method of claim 1, wherein said method further comprises regenerating a plant from said impacted plant cell.

10. The method of claim 4, wherein the said flow rate is between about 4 μl/minute and about 50 μl/minute.

11. The method of claim 10, wherein the said flow rate is between about 8 μl/minute and about 50 μl/minute.

12. The method of claim 6, wherein the said flow rate is between about 4 μl/minute and about 50 μl/minute.

13. The method of claim 12, wherein the said flow rate is between about 8 μl/minute and about 50 μl/minute.

14. The method of claim 1, wherein the said flow rate is between about 4 μl/minute and about 50 μl/minute.

15. The method of claim 14, wherein the said flow rate is between about 8 μl/minute and about 50 μl/minute.

16. The method of claim 1, wherein said one or more carbohydrates is sucrose.

* * * * *